United States Patent
Kalanovic et al.

[11] Patent Number: 5,827,301
[45] Date of Patent: Oct. 27, 1998

[54] DEVICE AND METHOD FOR INTRAOPERATIVE CALIBRATION OF A FUNDUS FOLD CUFF

[75] Inventors: Daniel Kalanovic, Tübingen; Gerd Haidle, Baltmannsweiler; Klaus Roth, Ofterdingen, all of Germany; Jacques Kayser, Ellange, Luxembourg; Gerhard Buess, Tübingen, Germany

[73] Assignee: Willy Rüsch AG, Kernen-Rommelshausen, Germany

[21] Appl. No.: 806,509

[22] Filed: Feb. 24, 1997

[30] Foreign Application Priority Data

Feb. 29, 1996 [DE] Germany .................. 196 07 575.0

[51] Int. Cl.$^6$ .................................................. A61B 17/00
[52] U.S. Cl. ........................... 606/148; 128/898; 604/96; 606/196
[58] Field of Search ..................... 606/191, 192, 606/196, 198, 148, 139; 604/96, 97, 98, 100, 104; 128/898

[56] References Cited

U.S. PATENT DOCUMENTS

| | | | |
|---|---|---|---|
| 3,049,125 | 8/1962 | Kriwkowitsch | 606/196 |
| 3,882,852 | 5/1975 | Sinnreich . | |
| 4,964,417 | 10/1990 | Peters . | |
| 5,338,302 | 8/1994 | Hasson | 604/105 |
| 5,352,199 | 10/1994 | Tower | 604/96 |
| 5,370,656 | 12/1994 | Shevel | 606/196 |
| 5,569,296 | 10/1996 | Marin et al. | 604/96 |
| 5,571,179 | 11/1996 | Manders et al. | 606/192 |
| 5,591,128 | 1/1997 | Sithole | 604/96 |

FOREIGN PATENT DOCUMENTS

| | | |
|---|---|---|
| 0610099 | 8/1994 | European Pat. Off. . |
| 790091 | 11/1935 | France . |

OTHER PUBLICATIONS

Database WPI,Section PQ, Week 9403, Derwent Publications Ltd., London & SU 1 785 663 A (Bashkir Med Inst.) 7 Jan. 1993.

Blum, A. L., Siewet, J.R. (eds): Refluxtherapie (Reflux therapy) Springer–Verlag Berlin, Heidelberg, New York, 1981, pp. 283–312, and pp. 381–385.

*Primary Examiner*—Michael Powell Buiz
*Assistant Examiner*—Vikki Trinh
*Attorney, Agent, or Firm*—Paul Vincent

[57] ABSTRACT

An apparatus (10) for intraoperative calibration of a fundus fold cuff comprises an inlet having lead (14) the end of which facing the patient being connectable to an inflatable balloon (13) and the other end of which facing away from the patient having means for inflation/deflation of the balloon 13 and for measurement of the internal pressure of the balloon (13). The balloon (13) has, at least in the inflated state, an outer contour defining a seating surface (16) and two raised humps (17) which are sidewardly bordered. Fundus portions are joined together to form a cuff surrounding the esophagus, and the properties of the cuff are determined by the forces exercised by the cuff on the balloon.

11 Claims, 1 Drawing Sheet

DEVICE AND METHOD FOR INTRAOPERATIVE CALIBRATION OF A FUNDUS FOLD CUFF

This application is based on German patent application 196 07 575.0 filed 29 Feb. 1996 the contents of which is hereby incorporated by reference.

BACKGROUND OF THE INVENTION

The invention concerns a device and a method for intraoperative calibration of a fundus fold cuff with an inlet lead having the end of which facing the patient being connectable to a pressure-sensitive body and the other end of which facing away from the patient being connectable to means for activation of the body and for measuring a pressure acting on the body.

A comparable device is known in the art in the form of an instrument which is introduced into the esophagus.

The transitional region between the esophagus and the stomach (cardia) is closed following swallowing by the action of muscles present in the lower region of the esophagus. These muscles (esophageal-sphincter) provide a system for regulation of the food passage out of the esophagus into the stomach. This regulation is effected by the helical-shaped travel and by the sphincter action of the horizontally disposed muscle fibres in the end portion of the esophagus as well as by the longitudinal loading of the of muscles.

In the event that the cooperating sphincter is weak, the open connection between the esophagus and the stomach can no longer be closed after ingestion and remains open. In this case, a so-called reflux disorder is present (reflux esophagitis) which causes discomfort to the patient e.g. inflammation of the esophagus mucous membrane, the eructation of acid, heartburn, pain when swallowing, as well as nausea.

For this reason, cardia sphincter insufficiency must be treated either internistically or operatively e.g. by effecting a cuff-shaped sewing of the esophagus with fundus folds. This leads to narrowing of the cardia esophagus section and produces an acute angle at the esophagus-gastrio transition region. Configuration of the sewn folds to form a cuff facilitates restoration of the closing mechanism at the esophagus-stomach interface.

Following an invasive action of this type the reduced opening between the esophagus and stomach interface can then once more be closed by the lower esophagus-sphincter, wherein the cuff pressure does not fall below a minimum value either during swallowing nor during temporal relaxation.

The cuff functions as a "one-way" valve to prevent all reflux. Although this is the intended goal of the operative procedure, it is not successfully achieved with the assistance of the conventional device since intraoperative measurement of pressure in the esophagus fails to properly calibrate the cuff. Even the smallest of esophagus wall irritations cause transfer of pressure variations to the conventional device. These pressure variations detected by the device therefore lead to insufficient determination of the properties of the cuff.

Unfortunately, improperly formed cuffs can lead to postoperative complications, frequently occurring ones of which are flatulence, dysphagia, and persistent reflux. A new operative procedure to change the cuff is, however, only possible in 40% of all cases, since the mutually connected folds tend to scar too strongly in the vicinity of their sewn ends and are extremely difficult to disjoin.

An intraoperative esophagus-manometry would appear to be unsuccessful, since the properties of fundus folds sewn into a cuff can only be detected to a limited extent.

The utilization of a particular cuff size is a first step in calibrating a cuff. Hereby it is significant how firmly or loosely the cuff is required to seat in order to be able to permanently close the transition region between the esophagus and the stomach after swallowing. Unsatisfactory treatment of cardia sphincter insufficiency is e.g. associated with formed cuffs which are too wide or too deep.

The absence of an objective method of calibration is therefore still a problem. An index finger of the surgeon probing the cuff is e.g. utilized to calibrate during open surgery.

A conventional possibility is to form the cuff via intraoperative measurement of the pressure on an instrument disposed in the vicinity of the cuff in the esophagus. Using this method the instrument is introduced into the esophagus up to the region of the cuff, is activated there, and the pressure acting on the instrument is measured. Since the measured pressure is disturbed by a plurality of factors primarily, however, by the position and orientation of the instrument in the vicinity of the cuff as well as by irritation of the esophagus, reliable and reproduceable results cannot be achieved using indirect measurements with conventional instruments. Furthermore, the formation of the cuff cannot be standardized utilizing the conventional instrument, since irritation of the esophagus leads to additional pressure fluctuation on the instrument.

It is therefore the purpose of the present invention to develop a device and a method to facilitate directed solution to the problem of cardia sphincter insufficiency, in that the properties of the operatively formed cuff in the vicinity of the esophagus-stomach interface can be determined more accurately and adjusted to the strength of the esophageal sphincter.

SUMMARY OF THE INVENTION

This purpose is achieved in accordance with the invention in that the body can be expanded to a predetermined volume and is preferentially embodied by a balloon and has an outer contour having, at least in the expanded state, a bulging seating surface which can be directly engaged by gathered portions of the fundus.

The creation of a body or balloon which can be directly placed between the esophagus and the cuff to fill a predetermined space allows for direct determination of forces transferred from the cuff to the body/balloon. The measured values can be applied taking into consideration the clinical state of a patient.

The bulging seating surface and sideward border allow for the fundus fold cuff to be fixed in position and disposed on the balloon in a reproduceable fashion. In this fashion, reliable measuring results can be achieved which can be evaluated in a directed fashion to facilitate determination of the interdependence between the pressure on the balloon and the muscular strength of the associated sphincter. The properties of the cuff formed by sewn fundus portions can be determined to thereby influence the properties of the cuff in a directed fashion.

The balloon body is manufactured from a thin latex-sheet. The balloon can transfer even small pressure variations to the measuring instrumentation attached thereto to thereby determine the effects of the operatively created cuff. The latex balloon has acceptable mechanical stability. A pressure-sensitive swell-body of this kind facilitates optimal formation of the cuff using objective criteria.

After formation of the cuff the balloon is introduced into the cuff and filled with gas up to a certain pressure. Subsequent venting of the balloon can facilitate improved positioning. Repeated increase in the inner pressure of the balloon up to unfolding of the balloon to a predetermined volume allows for subsequent correlation between the action of the cuff and the measured inner pressure. The special configuration of the outer contour of the balloon creates a defined and constant measuring field on the balloon. A defined separation of the raised humps selects a reproduceable length of sewn cuff region for evaluation, and the cuff cannot dislodge in response to increased internal pressure in the balloon. The balloon and the raised humps can be manufactured having different fundamental sizes so that the device best suited to a particular patient can be chosen in advance. A balloon size or swell-body size is preferentially utilized which can be expanded by a predetermined gas volume or to a predetermined volume.

In a particularly preferred embodiment, the cuff calibration device comprises a guide bushing through which the inlet lead can be introduced in the longitudinal direction and within which the inlet lead can be displaced, with the end of the bushing facing away from the patient being closed by a sealing cap. The guide bushing and the sealing cap can also be manufactured from a single piece.

In the event of a laparoscopic fundus fold, the balloon is disposed inside of the guide bushing in a folded-together state for introduction into the abdomen. The guide bushing is pushed into a trocar for facilitating entrance to the abdomen. The balloon is pressed or pushed out of the guide bushing in the abdomen and inflated under the cuff. The balloon can likewise be retracted into the guide bushing after deflation so that the device can once more be easily removed from the abdomen. In this fashion the device for cuff calibration in accordance with the invention is also suitable for minimally invasive surgery. Towards this end the guide bushing along with the balloon located therein is introduced via a conduit, for example a trocar, into a predetermined hollow region of the patient.

In an additional embodiment the sealing cap has an opening for introduction of an instrument or the like through the guide bushing. When not in use, the opening can be covered by a valve membrane so that an instrument can be easily introduced into the guide bushing with the device otherwise being sealed towards the outside. The device for cuff calibration facilitates the introduction of instruments other than the balloon into the stomach cavity to e.g. position the balloon.

It is advantageous to manufacture the guide bushing from a stably-shaped plastic and the sealing cap from silicone to facilitate sterilization of the device.

The above-mentioned purpose is also achieved by a method with which the stomach fundus is folded around the esophagus to form a cuff surrounding a body expandable to a predetermined volume (preferentially a balloon) with the body being connected to measuring instruments to measure and display the pressure directly exercised by the cuff on the expanded body or to pass same to additional devices for evaluation. After the properties of the cuff have been determined and, if necessary corrected via the expanded body disposed between the esophagus and the cuff, the volume of the body is reduced and same is removed from the abdomen. The body is preferentially a balloon made from an elastic material occupying the volume of a region between the cuff and the esophagus. Subsequent to initial establishment of this region, the pressure exercised by the cuff on the body is recorded and evaluated.

Arbitrary bodies can be utilized for pressure measurement which are expandable from a reduced size (volume) to an enlarged size (volume). The data recorded and measured in the expanded state of the body can be directly subject to digital analysis. This analysis determines the current state of the cuff and yields data which may suggest that a change in the cuff is indicated.

A method of this kind facilitates measurement of forces exercised by the cuff on the balloon in a direct fashion. In the event that a balloon, defined in the sideward direction by two raised humps, is displaced below the cuff into the hollow area up to the esophagus, a defined measuring field on the balloon is thereby obtained and a directed measurement of the internal pressure of the balloon is facilitated for a particular inner diameter of the formed cuff.

This correlation between the internal pressure of the balloon and the inner diameter of the cuff facilitates a directed elimination of the cardiac sphincter insufficiency to obviate new surgical procedures. The folds gathered to form a cuff are tied in a conventional fashion and the recorded measured values are evaluated in view of the clinical status of the patient.

In another variation of the method, the balloon is connected to measuring instruments via an inlet lead partially surrounded by an inlet bushing. Conventional minimally invasive surgical methods can be utilized to enter the stomach cavity via a trocar so that: a guide bushing and captured balloon can be pushed into the trocar with the balloon being positionable in the vicinity of the transition region between the esophagus and the stomach.

It is likewise advantageous to introduce additional instruments through the guide bushing into the hollow region of the body to assist in the positioning of the inserted balloon.

It is particularly advantageous when the cuff seats on a convex-shaped seating surface of the balloon. Another surface of the balloon which is diametrically opposed to the seating surface is concave and disposed on the outer wall of the esophagus. In this fashion the balloon in accordance with the invention can be positioned safely and the cuff can interlockingly cover the balloon. The concave surface of the balloon is preferentially adapted to an instrument positioned in the esophagus which splints the esophagus in the vicinity of the cuff. Pressure variations and the applied pressure of the cuff can be better determined and transmitted by the balloon, since the catheter forms an abutment.

In the event of a laparoscopic fundus fold, the balloon is accommodated in a guide bushing and the guide bushing is introduced into the abdomen through an opening. This opening is preferentially formed by a trocar. The balloon is pushed or pulled out of the guide bushing in the abdomen and inflated under the cuff.

It is particularly advantageous in association with laparoscopic fundus fold if the sideward humps have color distinguishable from the remaining portions of the balloon with the cuff being sewn between those sideward bumps. This color contrast of the sideward bumps with respect to the remaining portions of the balloon allows for better estimation or determination of distances.

The method in accordance with the invention and the device created therefor allow for intraoperative calibration of a cuff both in open surgery as well as in the event of a laparoscopic procedure using objective and reproduceable criteria which are not distorted by sphincter irritations.

Further advantages can be derived from the description of the accompanying drawing. The above mentioned features and those to be described further below can be utilized in accordance with the invention individually or collectively in arbitrary combination. The embodiments mentioned are not to be considered as exhaustive enumeration, rather have exemplary character. The invention is shown in the drawing and is described more closely with regard to an embodiment.

DESCRIPTION OF THE PREFERRED EMBODIMENT

Figure 1:
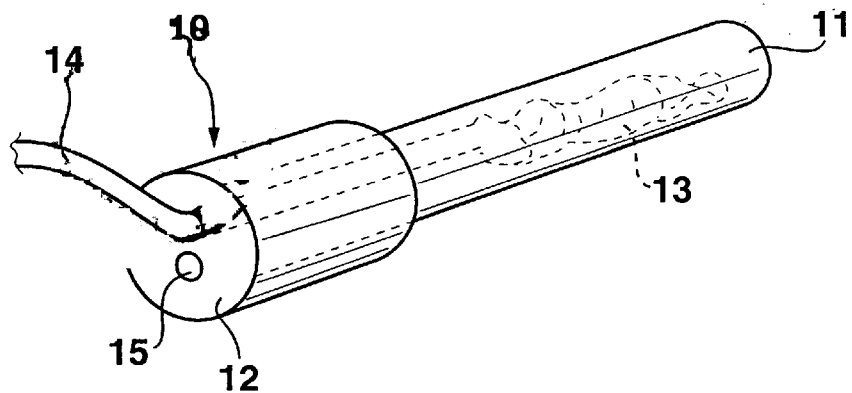
FIG. 1 shows a device for cuff calibration having a guide bushing containing a non-activated balloon.

The figures of the drawing show the object in accordance with the invention in a highly schematic fashion and are not necessarily to be taken to scale. The structural features are represented in the individual drawings in such a fashion that the construction of the apparatus and the shape of the balloon can be clearly shown.

FIG. 1 shows a perspective representation of a device for cuff calibration 10 which could be used for laparoscopic fundus fold applications. The device 10 consists essentially of a guide bushing 11 closed at one end by a sealing cap 12 and open at the other end. The sealing cap 12 can be manufactured from silicone and can tightly surround the guide bushing 11. In another embodiment, the sealing cap 12 and the guide bushing 11 can be manufactured as a single piece. The apparatus 10 is suitable for introduction into trocars utilized in endoscopic operations, preferentially 10–12 mm trocars. A balloon 13 is accommodated inside of the guide bushing 11 connected to an inlet lead 14 by means of which the balloon 13 can, using auxiliary means not shown in the figure, initially be pushed out of the guide bushing 11 and inflated. When the balloon 13 is completely within the guide bushing 11 the apparatus 10 prevents the possible occurrence of introductory resistance on the part of the balloon into the stomach cavity via the trocar. The device 10 further has a sealed opening 15 through which means for assisting positioning of the balloon 13 can be introduced or surgical instruments for other purposes.

Figure 2:
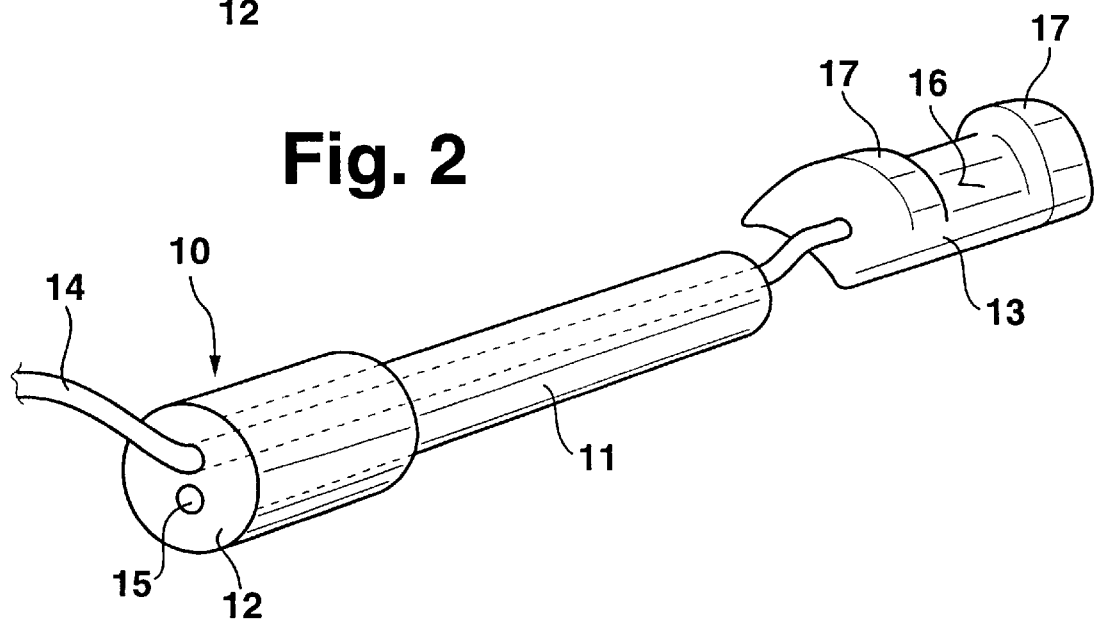
FIG. 2 shows the device according to FIG. 1 with the balloon activated outside of the guide bushing.

FIG. 2 shows the device 10 after exit of the balloon 13 out of the guide bushing 11 in the inflated state of the balloon 13. The balloon 13 is connected via the inlet lead 14 to means for facilitating inflation or deflation of the balloon 13. Towards this end the balloon 13 can be inflated in a directed fashion to a specific predetermined and measurable internal pressure.

The balloon 13, in its inflated state, has a characteristic outer contour in accordance with the invention for precise positioning in the vicinity of the transition region between the esophagus and the stomach. The formation of this outer contour guarantees a constant measuring field. The balloon 13 has a bulged seating surface 16 in the inflated state on which the fundus fold cuff seats. The balloon 13 has a concave surface diametrically opposed to the seating surface 16 which can adapt itself in a particularly advantageous fashion to the outer surface of the esophagus in the vicinity of the esophagus-stomach transition region. The seating surface 16 is sidewardly bordered by raised humps 17 so that the balloon 13 is securely positioned by the surroundingly engaging cuff. This is also possible in the event that only a small internal pressure is present within the balloon 13. The balloon 13 is manufactured from a highly elastic, tissue-compatible, and resistant material e.g. latex.

Figure 3:
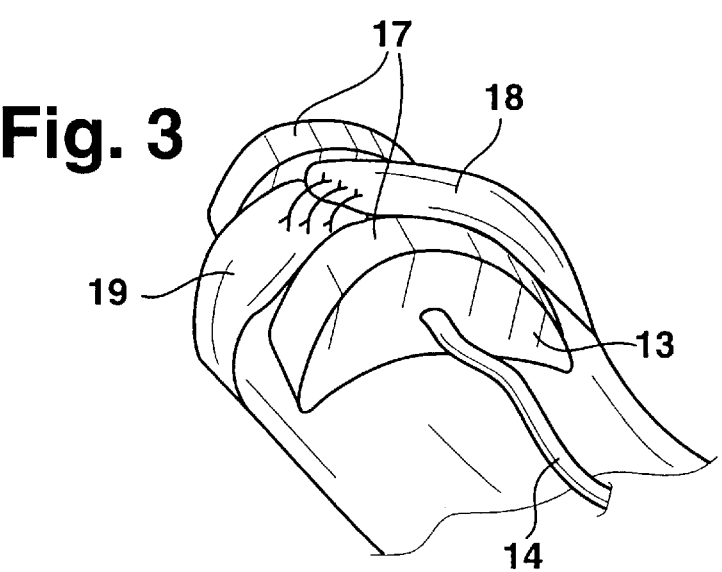
FIG. 3 shows the activated balloon according to FIG. 2 surrounded by a cuff of fundus folds.

FIG. 3 shows a perspective view of a use of the device 10 in accordance with the invention. The apparatus 10 is enlarged and represented in only a partially visible fashion. The balloon 13 and its inlet lead 14 can be recognized in the figure. Following a fundus fold procedure the fundus folds 18 and 19 (fundus portions) are drawn together to form a cuff which reduces the opening of the esophagus-stomach transitional region. Same represents an operative measure for overcoming cardiac sphincter insufficiency.

Since the balloon 13, in the inflated state, has humps 17, the cuff formed by the fundus folds 18 and 19 can be placed around the balloon 13 on the seating surface 16 (covered in the figure) and its position secured at this location. The bumps 17 have a color which is distinguishable from that of the remaining portions of the balloon 13.

The definition of the surface using bumps 17 facilitates a constant measuring field for the balloon 13 for measurement of a correlation between the balloon inner pressure and the strength of the cuff formed by the preferentially sewn fundus folds 18 and 19. The properties of the formed cuff can be checked in an intraoperative fashion and, using the known correlation, corrected to desired characteristic values.

Sundry manometers can be connected to the inlet lead 14 by means of which even the smallest of pressure variations in the balloon region can be detected and evaluated. It is also possible for the inlet leads 14 to be divided to facilitate inflation of the balloon via these inlet leads 14 and also for passing the inlet lead 14 to a pressure-sensitive or display apparatus through the switching of a valve.

We claim:

1. A device for intraoperative calibration of a fundus fold cuff of a patient being connectable to means for activation of the device and to means for pressure measurement, the device comprising:

an inlet lead having a first end facing away from the patient for connecting to the activation means and a second end facing toward the patient; and an expandable body for inflating to a predetermined volume, said body having an outer surface that has a convex-shaped seating surface directly surrounded by the fundus fold cuff, said seating surface being sidewardly bordered by two raised humps for fixedly holding the fundus fold cuff in an inflated state of said expandable body, wherein said second inlet lead end connects to said expandable body and to the pressure measurement means for measuring an internal pressure acting on said expandable body.

2. The device of claim 1, wherein said expandable body is a balloon.

3. The device of claim 1, further comprising a guide bushing for housing said inlet lead in a longitudinal direction which said inlet passes through said guide bushing, wherein, said bushing having a bushing end facing away from the patient includes a sealing cap, whereby said sealing cup covers said bushing end.

4. The device of claim 3, wherein said sealing cap has an opening for insertion of said inlet lead through said guide bushing.

5. A method for intraoperative calibration of a fundus fold cuff of a patient, the method using means for activation of a device for intraoperative calibration of the cuff, the activation means connectable to the cuff, the method also using means for pressure measurement, the method comprising the steps of:

placing a body of the device at a stomach-esophagus interface;

forming the cuff through folding a stomach fundus around an esophagus to surround said body;

expanding said body to a predetermined volume; and measuring a pressure directly exercised by the cuff on said expanded body.

6. The method of claim 5, wherein said body is bordered at sides by two raised humps, and said body is placed between the cuff and the esophagus.

7. The method of claim 5, wherein the cuff seats on a convex seating surface of said body and said body has a surface diametrically opposed to said seating surface which is concave and which is placed on an outer wall of the esophagus.

8. The method of claim 7, wherein said concave surface is adapted to an outer contour of an instrument placed in the esophagus.

9. The method of claim 5 for use in a laparoscopic fundus fold procedure, wherein said body is disposed in a guide bushing, introduced into an abdomen via an entrance, and displaced out of the guide bushing, and said body is inflated below the cuff.

10. The method of claim 6, wherein said cuff is sewn between said two raised humps, said two raised humps having a color which is distinguished from a color of remaining portions of said body.

11. The method of claim 9, wherein additional probes are introduced into the abdomen via said guide bushing and said entrance.

* * * * *